US010532192B2

(12) United States Patent
Hurley et al.

(10) Patent No.: US 10,532,192 B2
(45) Date of Patent: Jan. 14, 2020

(54) REGIONAL ANESTHESIA CATHETER WITH ANCHOR

(71) Applicant: Brigham and Women's Hospital, Inc., Boston, MA (US)

(72) Inventors: Ronald J. Hurley, Boston, MA (US); Roman Portnoy, Brookline, MA (US); James H. Philip, Chestnut Hill, MA (US)

(73) Assignee: BRIGHAM AND WOMEN'S HOSPITAL, INC., Boston, MA (US)

( * ) Notice: Subject to any disclaimer, the term of this patent is extended or adjusted under 35 U.S.C. 154(b) by 106 days.

(21) Appl. No.: 15/558,640

(22) PCT Filed: Mar. 15, 2016

(86) PCT No.: PCT/US2016/022428
§ 371 (c)(1),
(2) Date: Sep. 15, 2017

(87) PCT Pub. No.: WO2016/149247
PCT Pub. Date: Sep. 22, 2016

(65) Prior Publication Data
US 2018/0071497 A1    Mar. 15, 2018

Related U.S. Application Data

(60) Provisional application No. 62/133,783, filed on Mar. 16, 2015.

(51) Int. Cl.
*A61M 25/10*    (2013.01)
*A61L 29/02*    (2006.01)
(Continued)

(52) U.S. Cl.
CPC ............. *A61M 25/10* (2013.01); *A61L 29/02* (2013.01); *A61L 29/042* (2013.01); *A61L 29/06* (2013.01);
(Continued)

(58) Field of Classification Search
CPC .. A61M 25/02; A61M 25/10; A61M 25/0032; A61M 25/1002; A61M 25/0025;
(Continued)

(56) References Cited

U.S. PATENT DOCUMENTS

| 4,973,305 A | 11/1990 | Goltzer |
| 5,084,016 A | 1/1992 | Freeman |

(Continued)

FOREIGN PATENT DOCUMENTS

| EP | 0931559 A2 | 7/1999 |
| GB | 2333461 | 7/1999 |

OTHER PUBLICATIONS

Afshan G, et al. Appropriate length of epidural catheter in the epidural space for postoperative analgesia: evaluation by epidurography. Anaesthesia. Oct. 2011;66(10):913-8. PubMed PMID: 21851342.
(Continued)

*Primary Examiner* — Imani N Hayman
*Assistant Examiner* — Tiffany Legette
(74) *Attorney, Agent, or Firm* — Quarles & Brady LLP

(57) ABSTRACT

Embodiments of the invention provide a system and method for accessing an internal body region using a catheter. The catheter includes a catheter body and a medication lumen positioned within the catheter body for delivering medication to the internal body region. An inflation lumen is positioned within the catheter body. A balloon is in fluid communication with the inflation lumen, and the balloon is configured to move between a collapsed position and an expanded position as fluid enters the balloon through the (Continued)

inflation lumen. An anchor covers at least a portion of the balloon on an outer surface of the catheter body and includes a movable section with a first retracted position and a second deployed position. Upon inflation of the balloon, the movable section of the anchor moves radially outward from the first contracted position to the second deployed position to secure the catheter in the internal body region.

22 Claims, 4 Drawing Sheets

(51) Int. Cl.
*A61L 29/04* (2006.01)
*A61L 29/06* (2006.01)
*A61L 29/16* (2006.01)
*A61M 19/00* (2006.01)
*A61M 25/00* (2006.01)

(52) U.S. Cl.
CPC .............. *A61L 29/16* (2013.01); *A61M 19/00* (2013.01); *A61M 2025/0007* (2013.01); *A61M 2025/1086* (2013.01); *A61M 2202/048* (2013.01); *A61M 2202/0468* (2013.01)

(58) Field of Classification Search
CPC .... A61M 2025/007; A61M 2025/0008; A61M 2025/0293; A61M 2025/1086; A61M 2025/0143; A61M 2025/0147; A61M 2025/1088; A61M 2025/109; A61M 1/3613; A61M 19/00
See application file for complete search history.

(56) References Cited

U.S. PATENT DOCUMENTS

| 5,203,773 | A | | 4/1993 | Green |
| 5,344,439 | A | | 9/1994 | Otten |
| 5,378,230 | A | * | 1/1995 | Mahurkar ......... A61M 25/0023 604/264 |
| 6,377,849 | B1 | | 4/2002 | Lenarz |
| 6,605,055 | B1 | | 8/2003 | Sinofsky |
| 6,663,589 | B1 | * | 12/2003 | Halevy ................. A61M 25/04 604/103.06 |
| 7,063,714 | B2 | | 6/2006 | Dorros |
| 7,922,738 | B2 | | 4/2011 | Eichmann |
| 8,287,538 | B2 | | 10/2012 | Brenzel |
| 8,725,249 | B2 | | 5/2014 | Bar-Yoseph |
| 2003/0004460 | A1 | * | 1/2003 | Bedell ................ A61B 1/00082 604/95.04 |
| 2003/0040704 | A1 | | 2/2003 | Dorros |
| 2006/0253099 | A1 | | 11/2006 | Noone |
| 2008/0058757 | A1 | | 3/2008 | Pajunk |
| 2009/0171284 | A1 | * | 7/2009 | Burke ................ A61M 25/104 604/104 |
| 2012/0179122 | A1 | * | 7/2012 | Eilat ..................... A61F 9/0026 604/290 |
| 2013/0144272 | A1 | | 6/2013 | Cutie |
| 2013/0304180 | A1 | | 11/2013 | Green |
| 2014/0121583 | A1 | * | 5/2014 | Duncan ................ A61M 27/00 604/8 |
| 2014/0358123 | A1 | * | 12/2014 | Ueda ................ A61M 25/0097 604/510 |

OTHER PUBLICATIONS

Burstal R, et al. Epidural analgesia: prospective audit of 1062 patients. Anaesth Intensive Care. Apr. 1998;26 (2):165-72. PubMed PMID: 9564395.
Burstal R, et al. Subcutaneous tunnelling of epidural catheters for postoperative analgesia to prevent accidental lislodgement: a randomized controlled trial. Anaesth Intensive Care. Apr. 1998;26(2):147-51. PubMed PMID: 9564391.
Chadwick VL, et al. Epidural catheter migration: a comparison of tunnelling against a new technique of catheter fixation. Anaesth Intensive Care. Oct. 2003;31(5):518-22. PubMed PMID: 14601274.
Clark MX, et al. The effect of the Lockit epidural catheter clamp on epidural migration: a controlled trial. Anaesthesia. Sep. 2001;56(9):865-70. PubMed PMID: 11531673.
Davies R, et al. Epidural catheters Breaking and extraction forces. Anaesthesia. Oct. 1993;48(10):900-1. PubMed PMID: 8238836.
Duff P, et al. Ambulatory postoperative ward-based epidural analgesia: a retrospective review of 1,147 cases. Ir J Med Sol. Mar. 2013;182(1):139-41. PubMed PMID: 22941496.
Hermanides J, et al. Failed epidural: causes and management. Br J Anaesth. Aug. 2012;109(2):144-54. PubMed PMID: 22735301.
Horlocker TT. Regional anaesthesia in the patient receiving antithrombotic and antiplatelet therapy. Br J Anaesth. Dec. 2011;107 Suppl 1:196-106. PubMed PMID: 22156275.
International Search Report and Written Opinion for application PCT/US2016/022428, dated Jun. 9, 2016, 16 pages.
Königsrainer I, et al. Audit of motor weakness and premature catheter dislodgement after epidural analgesia in major abdominal surgery. Anaesthesia. Jan. 2009;64(1):27-31. PubMed PMID: 18671685.
McLeod G, et al. Postoperative pain relief using thoracic epidural analgesia: outstanding success and disappointing failures. Anaesthesia. Jan. 2001;56(1):75-81. PubMed PMID: 11167441.
Motamed C, et al. An analysis of postoperative epidural analgesia failure by computed tomography epidurography. Anesth Analg. Oct. 2006;103(4):1026-32. PubMed PMID: 17000824.
Richter A, et al. Effect of long-term thoracic epidural analgesia on refractory angina pectoris: a 10-year experience. J Cardiothorac Vasc Anesth. Oct. 2012;26(5):822-8. PubMed PMID: 22480635.
Ruppen W, et al. Incidence of epidural haematoma and neurological injury in cardiovascular patients with epidural analgesia/anaesthesia: systematic review and meta-analysis. BMC Anesthesiol. Sep. 12, 2006;6:10. PubMed PMID: 16968537; PubMed Central PMCID: PMC1586186.
Sim WS, et al. The influence of patient position on withdrawal force of thoracic epidural catheters. Anaesthesia. Jan. 2012;67(1):19-22. PubMed PMID: 21972884.
Tsui SL, et al. Delayed epidural catheter removal: the impact of postoperative coagulopathy. Anaesth Intensive Care. Oct. 2004;32(5):630-6. PubMed PMID: 15535484.
Vandermeulen EP, et al. Anticoagulants and spinal-epidural anesthesia. Anesth Analg. Dec. 1994;79(6):1165-77. PubMed PMID: 7978443.

* cited by examiner

REGIONAL ANESTHESIA CATHETER WITH ANCHOR

CROSS-REFERENCE TO RELATED APPLICATIONS

This application represents the national stage entry of PCT International Application PCT/US2016/022428 filed Mar. 15, 2016, which claims benefit of U.S. Provisional Application 62/133,783 filed Mar. 16, 2015, all of which is incorporated herein in its entirety by reference.

STATEMENT REGARDING FEDERALLY SPONSORED RESEARCH

Not Applicable.

BACKGROUND OF THE INVENTION

Millions of epidural and peripheral nerve block anesthesia catheters are placed in the United States each year for indications including labor analgesia, open abdominal, thoracic, vascular, and orthopedic surgery, chronic and acute pain control, and many others. Epidural and peripheral nerve block anesthesia catheters are often utilized up to 7-10 days to provide pain relief in a post-operative patient. Unfortunately, the failure rate of epidural analgesia is reported to be as high as 30%.

Epidural and peripheral nerve block anesthesia catheters are fraught with a high rate of inadvertent dislodgement. Thus, one of the most common causes of epidural and peripheral nerve block catheter failure is catheter dislodgment, comprising 45% of all failures in one study, and 57% of all catheter related complications in another study. The overall rate of accidental catheter dislodgement depends on duration, depth of insertion, and external fixation technique, varying widely from as low as 3% to as high as 53% in some studies. Catheter dislodgement may effectively expose the patient to the risks introduced in epidural or peripheral nerve block placement while truncating the benefit, and potentially increasing the risk of epidural hematoma formation.

Several external catheter fixation techniques have been used in an effort to prevent catheter dislodgement and/or catheter migration. These techniques have included subcutaneous tunneling, suturing, and external fixation devices. However, none of these external fixation techniques have been widely adopted due to poor efficacy, concerns over infectious risk, and patient comfort.

Each time an epidural or peripheral catheter is inadvertently dislodged, man-power and materials are wasted in order to replace it. The patient often experiences worsened pain, which often is treated with systemic opiates, that have been shown to delay return of bowel function and lengthen hospital stay. In addition, patient satisfaction, an outcome measure which may likely become tied to reimbursement in the future, can decline when pain is inadequately controlled. Moreover, an inadvertently dislodged catheter in a coagulopathic or deliberately anti-coagulated patient can cause epidural hematoma formation, which is a complication that can be costly to treat.

Another key patient population where catheter dislodgement can carry significant hidden costs, both to the patient and facility, is the thoracic surgery patient. Thoracic surgery patients are often pulmonary cripples who are reliant on epidural analgesia to be able to take adequate tidal volumes with each breath. Loss of epidural analgesia in such patients can cause inability to wean ventilator support, or trigger the need for re-intubation, with all of the associated subsequent complications.

Lastly, long-term epidural catheters, such as those used for chronic pain in cancer patients, often have a higher rate of dislodgement. At the same time, this patient population would arguably have the highest costs associated with catheter dislodgment, as they are typically located away from the hospital, are difficult to transport, and have the most severe forms of pain.

Therefore, a catheter for accessing an internal body region (i.e., an epidural space, nerve region, or the like) is needed that overcomes the above limitations.

SUMMARY OF THE INVENTION

The present invention relates to a system and method for accessing an internal body region, such as the epidural space or a nerve region, using a catheter characterized by an inflatable anchor to secure the catheter in the internal body region. The inflatable anchor is coupled to a distal end of the catheter tip to provide an internal fixation system for the catheter. The catheter may be utilized in at least hepatic, gastro-intestinal, orthopedic, obstetric/gynecological, vascular, and thoracic surgeries to inhibit catheter dislodgement and migration.

Some aspects of the invention provide a system for accessing an internal body region using a catheter. The catheter includes a catheter body and a medication lumen positioned within the catheter body for delivering medication to the internal body region. An inflation lumen is positioned within the catheter body. A balloon is in fluid communication with the inflation lumen, and the balloon is configured to move between a collapsed position and an expanded position as fluid enters the balloon through the inflation lumen. An anchor covers at least a portion of the balloon on an outer surface of the catheter body and includes a movable section with a first retracted position and a second deployed position. Upon inflation of the balloon, the movable section of the anchor moves radially outward from the first contracted position to the second deployed position to secure the catheter in the internal body region.

In one version of this aspect of the invention, the anchor includes a plurality of movable sections configured to move between the first retracted position and the second deployed position.

In one version of this aspect of the invention, each of the plurality of movable sections is defined by a longitudinal section having a length between about 0.15 inches and about 0.18 inches.

In one version of this aspect of the invention, the medication lumen is defined by an arcuate shape in cross-section to decrease an injection pressure required by the medication lumen.

In one version of this aspect of the invention, the medication delivered to the internal body region includes at least one of saline and an anesthetic solution.

In one version of this aspect of the invention, the inflation lumen is coupled to a fluid source for delivering at least one of air, gas and liquid to the balloon.

In one version of this aspect of the invention, the anchor comprises at least one of a silicon, polyurethane, nylon, latex, and polyisoprene material.

In one version of this aspect of the invention, the anchor is provided in the form of a sheath and is adhesively coupled to the catheter body In one version of this aspect of the invention, the movable section of the anchor has a bowed shape when in the second deployed position.

In one version of this aspect of the invention, the movable section of the anchor includes two segments meeting at a flexible joint when in the second deployed position.

In one version of this aspect of the invention, the movable section of the anchor includes two segments meeting at a flexible joint when in the second deployed position.

In one version of this aspect of the invention, the movable section of the anchor has a symmetrical shape about the catheter body when in the second deployed position.

In one version of this aspect of the invention, the movable section of the anchor has an asymmetrical shape about the catheter body when in the second deployed position.

In one version of this aspect of the invention, the internal body region is an epidural space; and wherein the catheter is an epidural catheter for accessing the epidural space.

In one version of this aspect of the invention, the internal body region is a nerve region; and wherein the catheter is a peripheral nerve catheter for accessing the nerve region.

In another aspect, the invention provides a method for accessing an internal body region using a catheter. The method includes inserting a catheter body into the internal body region and delivering a medication to the internal body region through a medication lumen positioned within the catheter body. A balloon surrounding the catheter body is inflated from a collapsed position to an expanded position as fluid enters the balloon through an inflation lumen in fluid communication therewith. Upon inflation of the balloon, an anchor having a movable section is configured to move from a first retracted position to a second deployed position to cause the movable section of the anchor to move radially outward to secure the catheter in the internal body region.

In one version of this aspect of the invention, the anchor includes a plurality of movable sections configured to move between the first retracted position and the second deployed position.

In one version of this aspect of the invention, the movable section of the anchor has a bowed shape when in the second deployed position.

In one version of this aspect of the invention, the movable section of the anchor includes two segments meeting at a flexible joint when in the second deployed position.

In one version of this aspect of the invention, the movable section of the anchor includes two outwardly inclined segments meeting at a flexible joint when in the second deployed position.

In one version of this aspect of the invention, the movable section of the anchor has a symmetrical shape about the catheter body when in the second deployed position.

In one version of this aspect of the invention, the movable section of the anchor has an asymmetrical shape about the catheter body when in the second deployed position.

In one version of this aspect of the invention, the internal body region is an epidural space; and wherein the catheter is an epidural catheter for accessing the epidural space.

In one version of this aspect of the invention, the internal body region is a nerve region; and wherein the catheter is a peripheral nerve catheter for accessing the nerve region.

These and other features, aspects, and advantages of the present invention will become better understood upon consideration of the following detailed description, drawings, and appended claims.

DETAILED DESCRIPTION OF THE INVENTION

Figure 1:
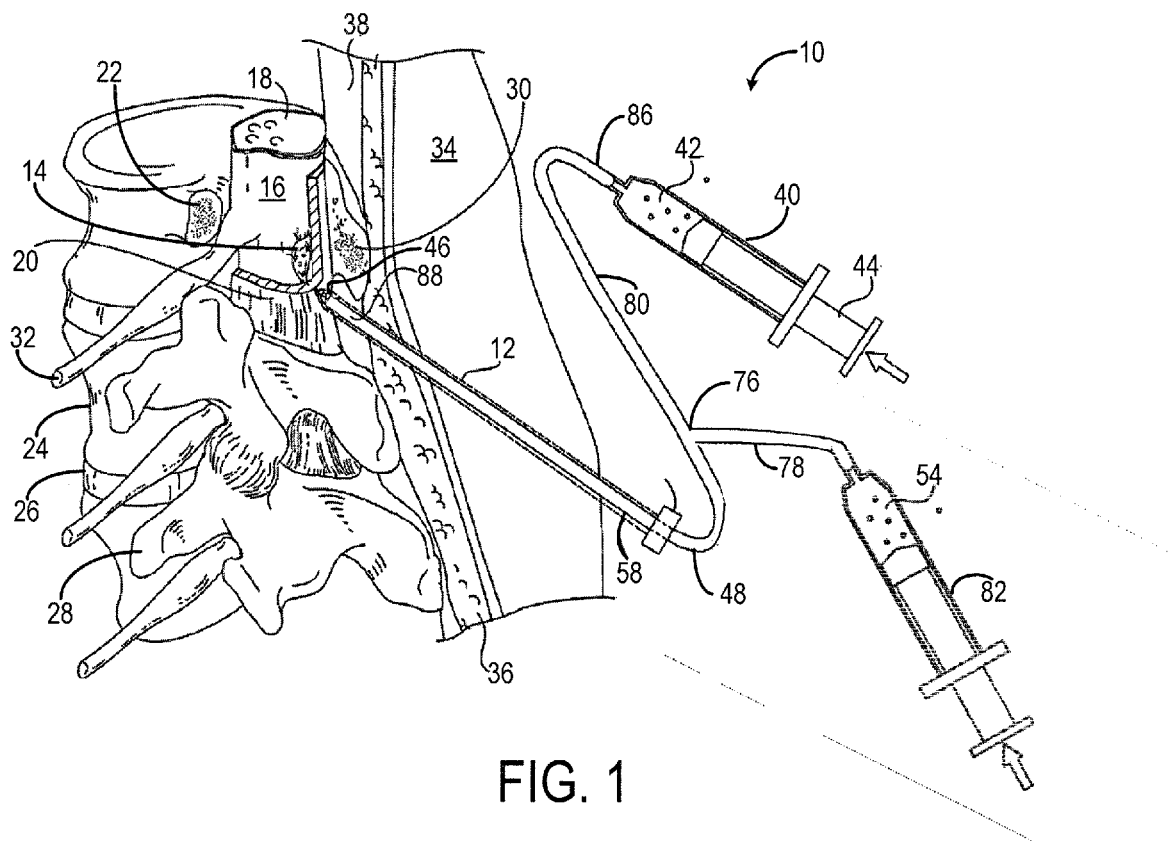
FIG. 1 is a perspective view of an example catheter accessing an epidural space and surrounding anatomical structures according to one embodiment of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Figure 2:
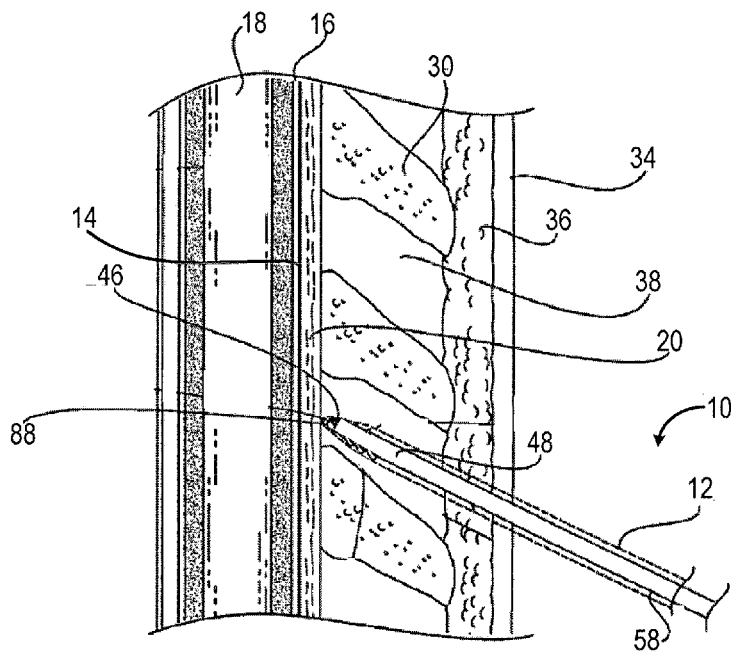
FIG. 2 is an enlarged perspective view of the catheter of FIG. 1 accessing the epidural space.

FIGS. 1-2 illustrate an example catheter 10 being inserted through a delivery needle 12 into an internal body region 14, such as an epidural space. As previously described, accessing the epidural space 14 can be challenging. The epidural space 14 is a potential space that is generally collapsed and enlarges when the tissues that bound it are separated. FIGS. 1 and 2 illustrate the tissues that define the epidural space 14 including the dura mater 16 (or dura) which is a protective covering that sheaths a spinal cord 18, a ligamentum flavum 20 which is a ligament adjacent to the dura 16 that runs longitudinally along the spinal column, and the bony sides of the vertebral canal. Other anatomical structures near the epidural space 14 illustrated in FIGS. 1 and 2 include a pedicle 22, a vertebral body 24, an intervertebral disc 26, transverse process 28, a spinous process 30 and a spinal nerve root 32.

To access the epidural space 14, a patient is positioned either seated or on their side and instructed to flex their back outward to maximize spacing between the outer vertebral components. The spinous processes 30 are palpated, and the location of the interlaminar space is estimated. A needle trajectory is then chosen by the anesthesiologist and the delivery needle 12, such as a Tuohy needle, is inserted in the midline. The delivery needle 12 includes a hollow lumen to allow for placement of the catheter 10 through which pain medication can be administered, as will be described in further detail below. As the delivery needle 12 is advanced, it passes through the patient's skin 34, soft tissue 36, interspinous ligament 38, and the ligamentum flavum 20 then ideally stops in the epidural space 14.

Prior to encountering the ligamentum flavum 20, a syringe 40 filled with air or saline 42, for example, is attached to the delivery needle 12. The needle 12 then is advanced slowly and gentle pressure is maintained on the syringe plunger 44 to assess the resistance to flow at a tip 46 of the delivery needle 12. A loss of resistance to flow, as assessed through subjective feel when the air or fluid 42 is ejected from the syringe 40, indicates that the needle 12 has passed through the ligamentum flavum 20 into the epidural space 14. The delivery needle 12 is held in position to allow placement of the catheter 10 then withdrawn from the epidural space 14 over the catheter 10.

Figure 3:
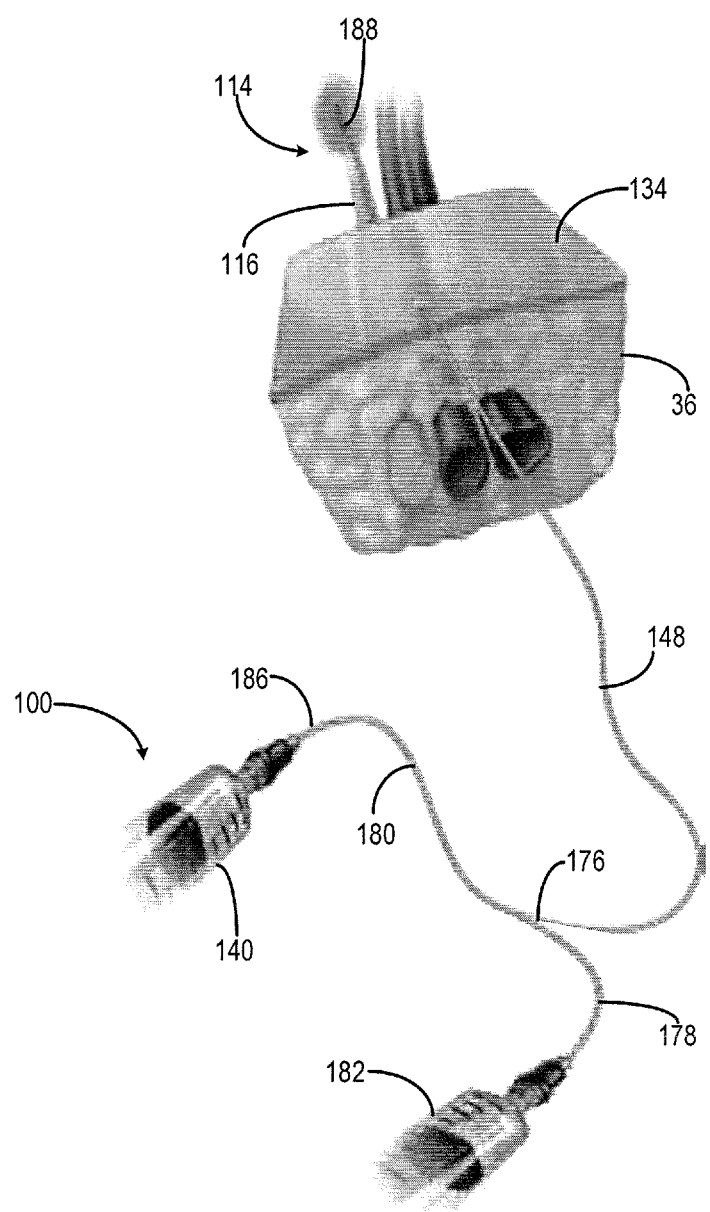
FIG. 3 is a perspective view of an example catheter accessing a nerve region and surrounding anatomical structures according to another embodiment of the present invention.

Although the above described catheter was described as an epidural catheter for accessing the epidural space 14, the catheter 10 may also be a peripheral nerve catheter 100, as shown in FIG. 3, for accessing a nerve region 114. The peripheral nerve catheter 100 is substantially the same as the epidural catheter 10. Therefore similar reference numerals are used to describe the catheter. The peripheral nerve catheter 100 can be placed at several different sites in the body, abutting major nerves 116 (i.e., brachial plexus, femoral, sciatic nerve, and the like) which innervate limbs, or more central regions (i.e., intercostals, paravertebral, transversus abdominis plane nerves innervating ribs, chest, abdomen), to deliver a continuous flow of local anesthetic for prolonged pain relief. An ultrasound probe is placed in the region of interest, the nerve 116 is identified, the nerve block needle is inserted under ultrasound guidance, puncturing through several layers of fat, muscle, and fascia, until the nerve 116 is reached under real-time ultrasound visualization. Once the desired needle location is achieved, a pocket of local anesthetic is created by injecting directly through the needle, then the block catheter 100 is threaded through the needle into the space directly next to the nerve 116. The needle is removed over the catheter 100, leaving the catheter 100 in place, and the catheter 100 is internally secured, as will be described in further detail below, to provide resistance against catheter 100 dislodgement by lodging against the inner most fascial plane surrounding the nerve 116.

Figure 4:
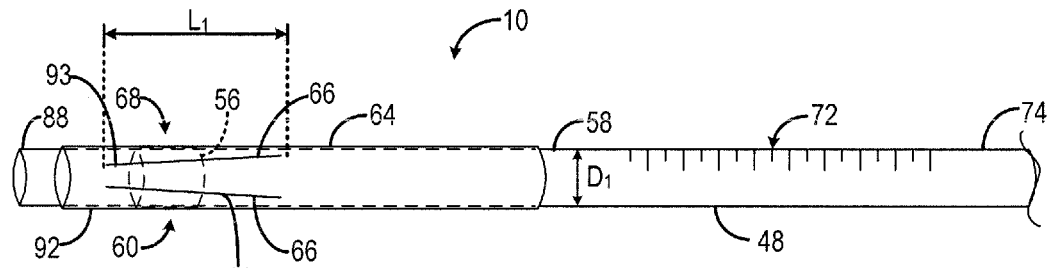
FIG. 4 is a side perspective view of the example catheter in a contracted position according to one embodiment of the present invention.
Figure 5:
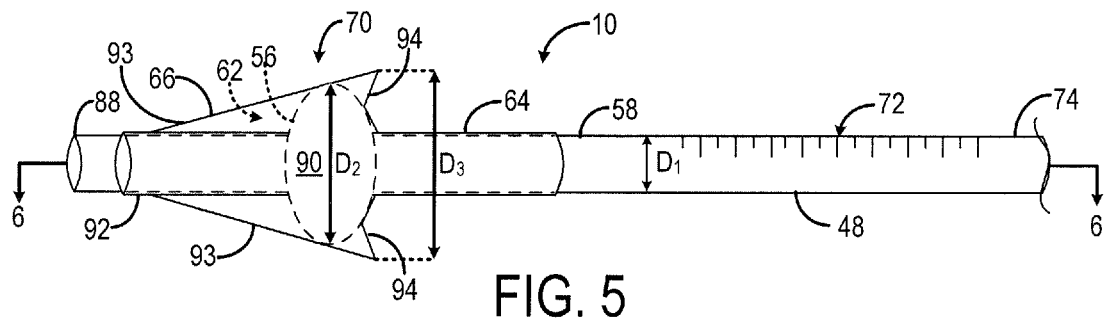
FIG. 5 is a side perspective view of the example catheter of FIG. 4 in a deployed position.
Figure 6:
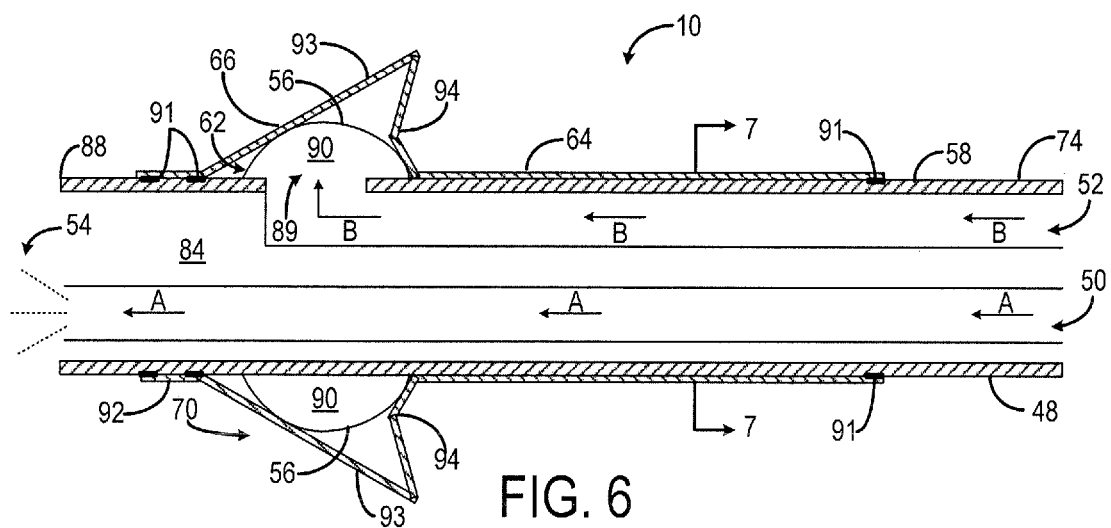
FIG. 6 is a side cross-sectional view of the example catheter of FIG. 5 taken about line 6-6.

Turning now to FIGS. 4, 5 and 6, embodiments of the catheter 10 will be described in greater detail. Generally, the catheter 10 is a regional anesthesia catheter including a catheter body 48 having positioned therein a medication lumen 50 and an inflation lumen 52. The medication lumen 50 is capable of delivering medication 54, such as saline or an anesthetic solution, to the internal body region 14 or 114 (i.e., the epidural space or nerve region). The inflation lumen 52 is in fluid communication with a balloon 56 that surrounds a portion of an outer surface 58 of the catheter body 48. As fluid enters the balloon 56 through the inflation lumen 52, the balloon 56 can move between a collapsed position 60 (see FIG. 4) and an expanded position 62 (see FIGS. 5 and 6). The catheter 10 further includes an anchor 64, which may be provided in the form of a sheath that covers a portion of the balloon 56 on the outer surface 58 of the catheter body 48. The anchor 64 may include a movable section 66 that moves radially outward from a retracted position 68 (see FIG. 4) to a deployed position 70 (see FIGS. 5 and 6) upon inflation of the balloon 56 to secure the catheter 10 within the internal body region 14 and reduce inadvertent catheter dislodgement, compared to conventional regional anesthesia catheters.

Turning to FIG. 4, the catheter body 48 may be cylindrical in shape and have an overall length of about 36 inches, however, the catheter body 48 may be characterized by any suitable length. In one non-limiting example, the external diameter $D_1$ of the catheter body 48 may be between about 0.035 inches and about 0.036 inches. In one example, the catheter body 48 is made from a polyether block amide material (e.g., PEBAX). The outer surface 58 of the catheter body 48 may include measurement markings 72 to provide an indication of insertion depth of the catheter 10 in the internal body region 14. As shown in FIG. 1, the catheter body 48 is bifurcated at a junction 76 into a medication lumen body 78 and an inflation lumen body 80 to house the medication lumen 50 and the inflation lumen 52, respectively, at a distal end 74 of the catheter body 48. Thus, the medication lumen 50 is fluidly coupled to a syringe 82 filled with the medication 54 for delivery into the internal body region 14. Similarly, the inflation lumen 52 is fluidly coupled to the syringe 40 filled with air, gas, or liquid 42 for delivery into the balloon 56.

Turning to FIG. 6, the catheter body 48 defines an internal passageway 84 at the distal end 74 in which the medication lumen 50 and the inflation lumen 52 are both disposed in. The medication lumen 50 is utilized to inject the medication 54, such as saline or an anesthetic solution, in the direction indicated by arrows A, from the syringe 82 to a tip 88 of the catheter body 48 and into the internal body region 14. Similarly, the inflation lumen 52 is utilized to inject air, gas, or liquid, for example, in the direction indicated by arrows B, from the syringe 40 to the enclosed balloon 56. The tip 88 of the catheter body 48 and the tip of the medication lumen 50 may be flexible in order to inhibit perforation of the dura 16 in the epidural space 14 (see FIG. 1), for example, or surrounding vessels in the nerve region 114 (see FIG. 3).

Figure 7:
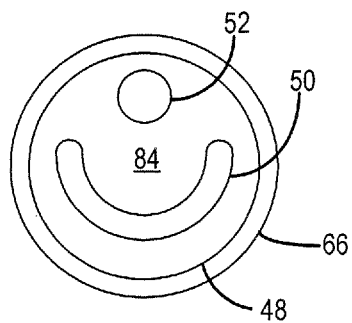
FIG. 7 is a cross-sectional view of the example catheter of FIG. 6 taken about like 7-7.

In some embodiments, the medication lumen 50 is defined by an arcuate shape in cross-section, as shown in FIG. 7, in order to decrease an injection pressure required by the medication lumen 50. Alternatively, the medication lumen 50 may be defined by any other shape in cross-section that provides a suitable injection pressure for the medication lumen 50. The inflation lumen 52 is defined by a circular shape in cross-section, as shown in FIG. 7, such that the lumens 50, 52 are arranged in a "smile" configuration in order to maximize the cross sectional area of the medication lumen 50 and decrease the required injection pressure, as just described. Alternatively, the injection lumen 50 may be defined by any suitable shape in cross-section.

Returning to FIG. 4, the balloon 56 is positioned at the distal end 74 of the catheter body 48 near the tip 88, and surrounds a portion of the outer surface 58 of the catheter body 48. In the collapsed position 60, the balloon 56 is substantially flush with the outer surface 58 of the catheter body 48. As air, gas, or liquid, for example, is injected into the inflation lumen 52, the balloon 56 moves from the collapsed position 60, as shown in FIG. 4, to the expanded position 62, as shown in FIGS. 5 and 6. An opening 89 is provided on the wall of the catheter body 48, as shown in FIG. 6, to allow fluid to pass from the inflation lumen 52 to an interior space 90 of the enclosed balloon 56. Inflation of the balloon 56 may be performed using the syringe 40 with a valve to maintain pressure. Additionally, or alternatively, the catheter 10 may incorporate a simple, disposable inflation device incorporated into the hub at a proximal end 86 of the inflation lumen body 80 (see FIG. 1).

In the expanded position 62, the balloon 56 may have a diameter $D_2$ of about 4 millimeters, as shown in FIG. 5, however the diameter $D_2$ is not limited to this dimension. As the balloon 56 expands from the collapsed position 60 to the expanded position 62, the anchor 64 moves from the retracted position 68 (see FIG. 4) to the deployed position 70 (see FIGS. 5 and 6). In the deployed position 70, the anchor may have a diameter $D_3$ of about 6 millimeters, however any suitable diameter $D_3$ may be provided to inhibit the internal tip 88 of the catheter body 48 from dislodging out of the internal body region 14 of the patient. Thus, the catheter 10 provides an improved fixation technique for epidural catheters and peripheral nerve catheters and can reduce inadvertent catheter dislodgement compared to conventional catheters. In addition, the catheter 10 may help to limit the occurrence of epidural hematoma, for example, by reducing catheter dislodgment and thus limiting hematoma formation in the setting of coagulopathy or deliberate anticoagulation.

The anchor 64 may be provided in the form of a sheath, as shown in FIG. 4, that covers the balloon 56 and a portion of the catheter body 48 at the distal end 74. In one example, the anchor 64 is made from a low durometer, high elasticity, resilient and biologically inert material. For example, the anchor 64 can be made from silicon, polyurethane, nylon, latex, polyisoprene, polyethylene terephthalate (PET), or the like. An adhesive 91, such as cyanoacrylate, may be provided on the outer surface 58 of the catheter body 48 to secure the anchor 64 thereto, as shown in FIG. 6. The adhesive 91 may be placed in pre-determined intervals along the outer surface 58 of the catheter body 48 or, alternatively, the adhesive 91 may be applied as a continuous thin film along the outer surface 58 of the catheter body 48, so long as the proximal end of the anchor 64 can freely move to allow the anchor 64 to move between the retracted position 68 and the deployed position 70. The adhesive 91 may reduce disruption of the bonding between the anchor 64 and the catheter body 48, which could lead to a lower extraction force.

Referring to FIGS. 4-6, the anchor 64 includes one or more movable sections 66 that move between the retracted position (see FIG. 4) and the deployed position 70 (see FIGS. 5 and 6) as the balloon 56 is inflated, while a relatively stationary section 92 at a distal portion of the anchor 64 remain secured to the catheter body 48. The movable sections 66 may be semi-rigid prongs 93, for example, that splay radially outward by inflation of the balloon 56 to combat inadvertent catheter dislodgement from within the internal body region 14.

In the embodiment shown in FIGS. 4-6, the movable section 66 includes two outwardly inclined prongs 93 that meet at a flexible joint 94 that extends radially outward when the movable section 66 is in the deployed position 70. Thus, the movable section 66 of the anchor 64 forms an asymmetrical shape about the catheter body 48 when in the deployed position 70. In other embodiments, the movable section 66 may include two or more outwardly inclined prongs 93 suitable for securing the catheter tip 88 within the internal body region 16.

Figure 8:
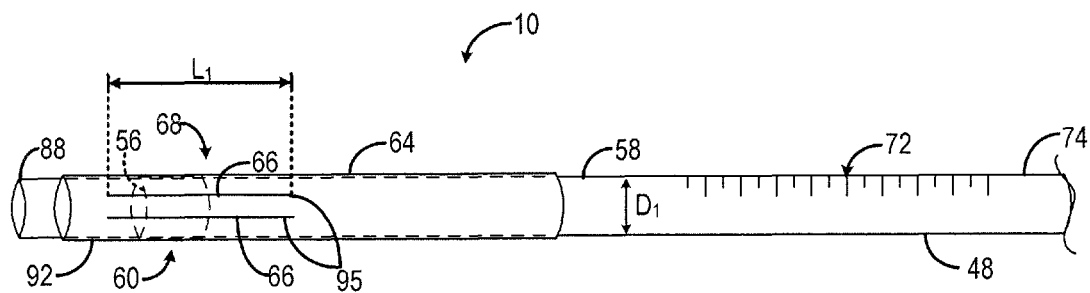
FIG. 8 is a side perspective view of the example catheter in a contracted position according to another embodiment of the present invention.
Figure 9:
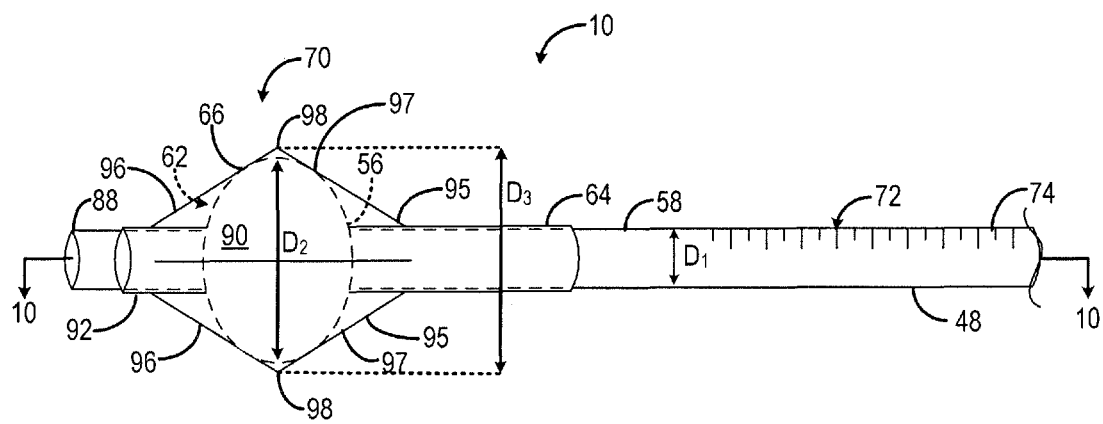
FIG. 9 is a side perspective view of the example catheter of FIG. 8 in a deployed position.
Figure 10:
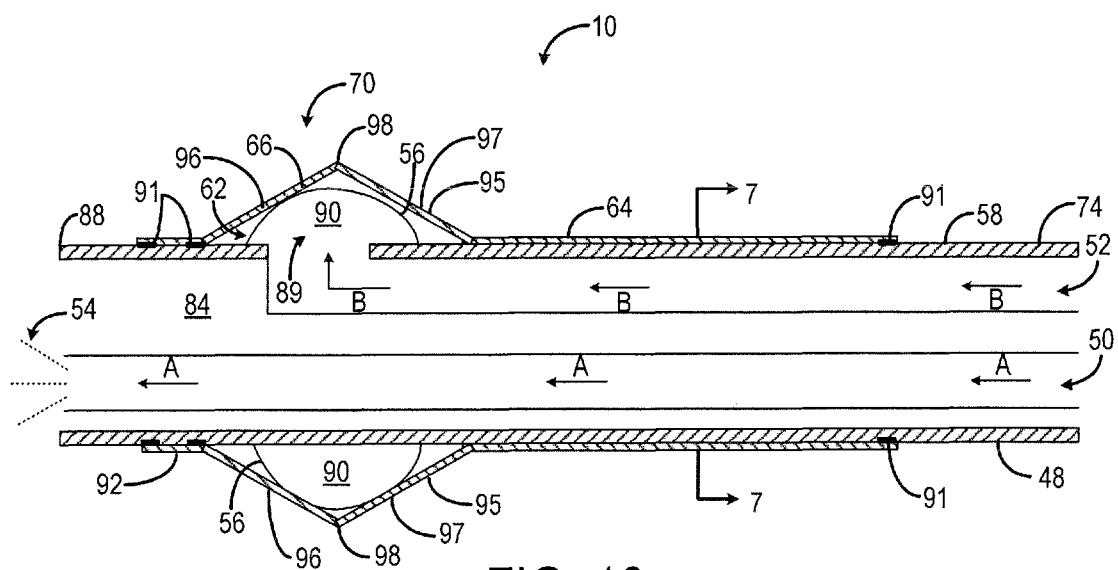
FIG. 10 is a side cross-sectional view of the example catheter of FIG. 9 taken about line 10-10.

In an alternative preferred embodiment, as shown in FIGS. 8, 9 and 10, the movable section 66 includes one or more prongs 95 each defined by a first segment 96 and a second segment 97. The embodiment shown in FIGS. 8, 9, and 10 is substantially the same as the embodiment shown in FIGS. 4-6, except for the movable section 66. Therefore similar reference numerals are used to describe the catheter in both embodiments. The first segment 96 and the second segment 97 meet at a flexible joint 98 positioned between the two segments 96, 97 when the movable section 66 is in the deployed position 70, as shown in FIGS. 9 and 10. Thus, the movable section 66 of the anchor 64 forms a symmetrical, bowed shape about the catheter body 48 when in the deployed position 70. In other embodiments, the movable section 66 may include two or more prongs 95 suitable for securing the catheter tip 88 within the internal body region 14.

In both embodiments, the prongs 93, 95 provide protection for the balloon 56 and added resistance against dislodgement. In one non-limiting example, each prong 93, 95 of the movable section 66 may have a length $L_1$ between about 0.15 inches and about 0.18 inches in the retracted position 68, as shown in FIGS. 4 and 8. The stationary sections 92 of the anchor 64 may extend between about 0.39 inches to about 0.79 inches along the catheter body 48 on the proximal side of the movable section 66. However, the length of the stationary sections 92 may be any suitable length to insure that a forward driving force is applied directly to the catheter body 48 by the operator's fingers, while threading the catheter 10. In some embodiments, a fine wire stylet may be threaded inside the medication lumen 50 of the catheter body 48 during catheter insertion, to provide added rigidity. The wire stylet may extend through the internal passageway 84 of the catheter body 48 and end several centimeters proximal to the tip 88 of the catheter body 48, to preserve the catheter's original softness at the tip 88.

During operation, the catheter 10, 100 may be inserted as a peripheral nerve catheter with or without ultrasound guidance, or an epidural catheter with or without fluoroscopic and epidurographic confirmation. Ultrasound guided peripheral nerve catheter placement may be carried out using any appropriate ultrasound machine under real-time guidance. The neurovascular bundle 116, as shown in FIG. 3, may be identified and the delivery needle 12 (e.g., a 17 g Tuohy needle) may be advanced using the standard "in-plane" method until the tip 46 is visualized just adjacent to the peripheral nerve being blocked. The tip 46 of the delivery needle 12 is designed to allow easy placement of the catheter 10, 100 with minimal trauma to tissues. At this point, a predetermined volume of saline may be injected through the delivery needle 12 to form a liquid pocket in the tissue, and the catheter 10, 100 is threaded through the delivery needle 12, approximately 2-3 cm beyond the tip 46 into the pocket. The delivery needle 12 may then be withdrawn. The anchor 64 is then deployed under real-time ultrasound guidance to confirm correct placement of the catheter 10, 100 and successful deployment of the anchor 64.

Thus, due to the internal nature of the anchor 64, minimal discomfort to the patient is caused and visualization of the insertion site is provided. Additionally, the internal nature of the anchor 64 generates an increased extraction force required to pull the catheter 10, 100 through fascia (connective tissue planes surrounding muscle and neurovascular bundles), or the ligamentum flavum 20. This increased extraction force (e.g., about 0.5 kilogram-force) can thereby decreases the chance of inadvertent catheter dislodgement, without increasing the risk of infection or discomfort to the patient.

This, the invention provides a system and method for accessing an internal body region, such as the epidural space or a nerve region, using a catheter characterized by an inflatable anchor to secure the catheter in the internal body region.

What is claimed is:

1. A catheter for accessing an internal body region, the catheter comprising: a catheter body; a medication lumen positioned within the catheter body for delivering a medication to the internal body region; an inflation lumen positioned within the catheter body; a balloon in fluid communication with the inflation lumen, the balloon configured to move between a collapsed position and an expanded position as fluid enters the balloon through the inflation lumen; an anchor covering at least a portion of the balloon on an outer surface of the catheter body, the anchor includes a plurality of movable sections configured to move between a first retracted position and a second deployed position, each anchor having a first connection to the catheter body distal to the balloon and a second connection to the catheter body proximal to the balloon; and wherein upon inflation of the balloon, the plurality of movable sections move radially outward from the first retracted position to the second deployed position to secure the catheter in the internal body region.

2. The catheter of claim 1, wherein each of the plurality of movable sections is defined by a longitudinal section having a length between about 0.15 inches and about 0.18 inches.

3. The catheter of claim 1, wherein the medication lumen is defined by an arcuate shape in cross-section to decrease an injection pressure required by the medication lumen.

4. The catheter of claim 1, wherein the medication for delivery to the internal body region includes at least one of saline and an anesthetic solution.

5. The catheter of claim 1, wherein the inflation lumen is coupled to a fluid source for delivering at least one of air, gas and liquid to the balloon.

6. The catheter of claim 1, wherein the anchor comprises at least one of a silicon, polyurethane, nylon, latex, and polyisoprene material.

7. The catheter of claim 1, wherein the anchor is provided in the form of a sheath and is adhesively coupled to the catheter body.

8. The catheter of claim 1, wherein the the plurality of movable sections have a bowed shape when in the second deployed position.

9. The catheter of claim 1, wherein each movable section of the the plurality of movable sections includes two segments meeting at a flexible joint when in the second deployed position.

10. The catheter of claim 1, wherein each movable section of the plurality of movable sections includes two outwardly inclined segments meeting at a flexible joint when in the second deployed position.

11. The catheter of claim 1, wherein each movable section of the plurality of movable sections has a symmetrical shape about the catheter body when in the second deployed position.

12. The catheter of claim 1, wherein each movable section of the plurality of movable sections has an asymmetrical shape about the catheter body when in the second deployed position.

13. The catheter of claim 1, wherein the internal body region is an epidural space; and wherein the catheter is an epidural catheter for accessing the epidural space.

14. The catheter of claim 1, wherein the internal body region is a nerve region; and wherein the catheter is a peripheral nerve catheter for accessing the nerve region.

15. A method for securing a catheter in an internal body region, the method comprising: the catheter comprising a catheter body and an anchor including a plurality of movable sections configured to move between a first retracted position and a second deployed position, each anchor having a first connection to the catheter body distal to the balloon and a second connection to the catheter body proximal to the balloon; inserting the catheter body into the internal body region; delivering a medication to the internal body region through a medication lumen positioned within the catheter body; and inflating a balloon surrounding the catheter body from a collapsed position to an expanded position as fluid enters the balloon through an inflation lumen in fluid communication therewith, wherein upon inflation of the balloon, the plurality of movable sections are configured to move from the first retracted position to the second deployed position, to cause the plurality of movable sections to move radially outward to secure the catheter in the internal body region.

16. The method of claim 15, wherein the plurality of movable sections have a bowed shape when in the second deployed position.

17. The method of claim 15, wherein each movable section of the plurality of movable sections includes two segments meeting at a flexible joint when in the second deployed position.

18. The method of claim 15, wherein each movable section of the plurality of movable sections includes two outwardly inclined segments meeting at a flexible joint when in the second deployed position.

19. The method of claim 15, wherein each movable section of the plurality of movable sections has a symmetrical shape about the catheter body when in the second deployed position.

20. The method of claim 15, wherein each movable section of the plurality of movable sections has an asymmetrical shape about the catheter body when in the second deployed position.

21. The method of claim 15, wherein the internal body region is an epidural space; and wherein the catheter is an epidural catheter for accessing the epidural space.

22. The method of claim 15, wherein the internal body region is a nerve region; and wherein the catheter is a peripheral nerve catheter for accessing the nerve region.

* * * * *